United States Patent [19]

Collier et al.

[11] Patent Number: 5,843,711

[45] Date of Patent: Dec. 1, 1998

[54] DIPHTHERIA TOXIN RECEPTOR-BINDING REGION

[75] Inventors: R. John Collier, Wellesley Hills, Mass.; David Eisenberg, Los Angeles, Calif.; Haian Fu, Allston, Mass.; Seunghyon Choe, Reseda, Calif.

[73] Assignees: The Regents of the University of California, Oakland, Calif.; The President and Fellows of Harvard College, Cambridge, Mass.

[21] Appl. No.: 552,248

[22] Filed: Nov. 2, 1995

Related U.S. Application Data

[63] Continuation of Ser. No. 119,316, Sep. 9, 1993, abandoned, which is a continuation of Ser. No. 881,394, May 6, 1992, abandoned.

[51] Int. Cl.$^6$ .................................................. C12N 15/00
[52] U.S. Cl. .................... 435/69.1; 435/69.3; 435/252.3; 435/320.1; 514/2; 536/22.1; 536/23.1; 536/23.2; 536/23.4; 536/23.7
[58] Field of Search .................................. 435/69.1, 69.3, 435/240.2, 252.3, 320.1; 514/2; 536/22.1, 23.1, 23.2, 23.4, 23.7

[56] References Cited

U.S. PATENT DOCUMENTS

| | | | |
|---|---|---|---|
| 4,709,017 | 11/1987 | Collier et al. | 530/350 |
| 4,950,740 | 8/1990 | Greenfield et al. | 530/350 |

FOREIGN PATENT DOCUMENTS

| | | |
|---|---|---|
| A-0332174 | 9/1989 | European Pat. Off. . |

OTHER PUBLICATIONS

Haynes (1993) Science. vol. 260, pp. 1279–1286.
Osterhaus et al. (1994) J. Infectious Diseases. vol. 170 (Suppl. 1):S42–55.
Orkin et al. (Dec. 1995) "Report and Recommendation of the Panel to Assess the NIH Investment in Research on Gene Therapy", Issued by the National Institutes of Health.
Stone "Biology approaches TeraPop Era" Science vol. 256, pp. 440–442 (1992).
Rolf et al. "Localization of the Diptheria . . . " JBC 265:13 pp. 7331–7337 May 5, 1990.
Anderson, P., 1983, Infection and Immunity, 39:233–238.
Anderson, P., et al., 1985, J Clin Invest, 76:52–59.
Arnon, R., 1986, Trends Biochem, 11:521–524.
Boquet, P., et al., 1981k Eur J Biochem, 121:93–98.
Eskola, J., et al., 1985, The Lancet, 1:1184–1186.
Giannini, G., et al., 1984, Nucleic Acids Research, 12:4063–4069.
Greenfield, L., et al., 1987, Science, 238:536–539.
Greenfield, L., et al., 1983, PNAS, 80:6853–6857.
McGill, S., et al., 1989, The EMBO J, 8:2843–2848.
Rolf, J.M. et al., Abstracts of the 91st Meeting of the Am Soc for Microbiol, 91:75, #B–296. (1991).
Rolf, J.M., et aL., 1991, 75th Annuan Meeting, FASEB J. 5:A821, #2619.
Tang, D., et al., 1992, Nature, 356:152–154.
Uchida, T., et al., 1971, Nature New Biology, 233:8–11.
Wen, Z., et al., 1991, The J of Biol Chem, 19:12289–12293.

Primary Examiner—Robert A. Wax
Assistant Examiner—Enrique D. Longton
Attorney, Agent, or Firm—Fish & Richardson, P.C.

[57] ABSTRACT

The invention features a polypeptide consisting of amino acids 379–535 of diphtheria toxin, and portions thereof. This region, shown by X-ray crystallographic analysis to comprise the receptor binding domain of diphtheria toxin, is used as an immunogen and clinical therapeutic against diphtheria.

15 Claims, 10 Drawing Sheets

```
                                      CCGGCGTTGCG
TAAAAACTCATTGAGGAGTAGGTCCCGATT  GGTTTTGCTAGTGAAGCTTAGCTAGCTTT

TAGCTTTACCTAATTATTTTATGAGTCCTG  GTAAGGGGATACGTTGTGAGCAGAAAACTG
                                              ValSerArgLysLeu
                                                          -21

GGCGCTGATGATGTTGTTGATTCTTCTAAA  TCTTTTGTGATGGAAAACTTTTCTTCGTAC
GlyAlaAspAspValValAspSerSerLys  SerPheValMetGluAsnPheSerSerTyr
                           10                               20

GGTACACAAGGAAATTATGACGATGATTGG  AAAGGGTTTTATAGTACCGACAATAAATAC
GlyThrGlnGlyAsnTyrAspAspAspTrp  LysGlyPheTyrSerThrAspAsnLysTyr
                           50                               60

GTCAAAGTGACGTATCCAGGACTGACGAAG  GTTCTCGCACTAAAAGTGGATAATGCCGAA
ValLysValThrTyrProGlyLeuThrLys  ValLeuAlaLeuLysValAspAsnAlaGlu
                           90                              100

GAAGAGTTTATCAAAAGGTTCGGTGATGGT  GCTTCGCGTGTAGTGCTCAGCCTTCCCTTC
GluGluPheIleLysArgPheGlyAspGly  AlaSerArgValValLeuSerLeuProPhe
                          130                              140

GTAGAACTTGAGATTAATTTTGAAACCCGT  GGAAAACGTGGCCAAGATGCGATGTATGAG
ValGluLeuGluIleAsnPheGluThrArg  GlyLysArgGlyGlnAspAlaMetTyrGlu
                          170                              180

TGCATAAATCTTGATTGGGATGTCATAAGG  GATAAAACTAAGACAAAGATAGAGTCTTTG
CysIleAsnLeuAspTrpAspValIleArg  AspLysThrLysThrLysIleGluSerLeu
                          210                              220

GAAAAAGCTAAACAATACCTAGAAGAATTT  CATCAAACGGCATTAGAGCATCCTGAATTG
GluLysAlaLysGlnTyrLeuGluGluPhe  HisGlnThrAlaLeuGluHisProGluLeu
                          250                              260

TGGGCAGTAAACGTTGCGCAAGTTATCGAT  AGCGAAACAGCTGATAATTTGGAAAAGACA
TrpAlaValAsnValAlaGlnValIleAsp  SerGluThrAlaAspAsnLeuGluLysThr
                          290                              300

GTTCACCACAATACAGAAGAGATAGTGGCA  CAATCAATAGCTTTATCGTCTTTAATGGTT
ValHisHisAsnThrGluGluIleValAla  GlnSerIleAlaLeuSerSerLeuMetVal
                          330                              340
```

FIG. 5a

```
TATCCAGTGGCTACACTCAGGTTGTAATGA  TTGGGATGATGTACCTGATCTGAGAGCGAT

CCCCATGTAACCAATCTATCAAAAAAGGGC  ATTGATTTCAGAGCACCCTTATAATTAGGA

TTTGCGTCAATCTTAATAGGGGCGCTACTG  GGGATAGGGGCCCCACCTTCAGCCCATGCA
PheAlaSerIleLeuIleGlyAlaLeuLeu  GlyIleGlyAlaProProSerAlaHisAla
                           -11                                -1

CACGGGACTAAACCTGGTTATGTAGATTCC  ATTCAAAAAGGTATACAAAAGCCAAAATCT
HisGlyThrLysProGlyTyrValAspSer  IleGlnLysGlyIleGlnLysProLysSer
                            30                                40

GACGCTGCGGGATACTCTGTAGATAATGAA  AACCCGCTCTCTGGAAAAGCTGGAGGCGTG
AspAlaAlaGlyTyrSerValAspAsnGlu  AsnProLeuSerGlyLysAlaGlyGlyVal
                            70                                80

ACTATTAAGAAAGAGTTAGGTTTAAGTCTC  ACTGAACCGTTGATGGAGCAAGTCGGAACG
ThrIleLysLysGluLeuGlyLeuSerLeu  ThrGluProLeuMetGluGlnValGlyThr
                           110                               120

GCTGAGGGGAGTTCTAGCGTTGAATATATT  AATAACTGGGAACAGGCGAAAGCGTTAAGC
AlaGluGlySerSerSerValGluTyrIle  AsnAsnTrpGluGlnAlaLysAlaLeuSer
                           150                               160

TATATGGCTCAAGCCTGTGCAGGAAATCGT  GTCAGGCGATCAGTAGGTAGCTCATTGTCA
TyrMetAlaGlnAlaCysAlaGlyAsnArg  ValArgArgSerValGlySerSerLeuSer
                           190                               200

AAAGAGCATGGCCCTATCAAAAATAAAATG  AGCGAAAGTCCCAATAAAACAGTATCTGAG
LysGluHisGlyProIleLysAsnLysMet  SerGluSerProAsnLysThrValSerGlu
                           230                               240

TCAGAACTTAAAACCGTTACTGGGACCAAT  CCTGTATTCGCTGGGGCTAACTATGCGGCG
SerGluLeuLysThrValThrGlyThrAsn  ProValPheAlaGlyAlaAsnTyrAlaAla
                           270                               280

ACTGCTGCTCTTTCGATACTTCCTGGTATC  GGTAGCGTAATGGGCATTGCAGACGGTGCC
ThrAlaAlaLeuSerIleLeuProGlyIle  GlySerValMetGlyIleAlaAspGlyAla
                           310                               320

GCTCAAGCTATTCCATTGGTAGGAGAGCTA  GTTGATATTGGTTTCGCTGCATATAATTTT
AlaGlnAlaIleProLeuValGlyGluLeu  ValAspIleGlyPheAlaAlaTyrAsnPhe
                           350                               360
```

FIG. 5b

```
GTAGAGAGTATTATCAATTTATTTCAAGTA  GTTCATAATTCGTATAATCGTCCCGCGTAT
ValGluSerIleIleAsnLeuPheGlnVal  ValHisAsnSerTyrAsnArgProAlaTyr
                           370                              380

GTTGAAGATTCGATAATCCGAACTGGTTTT  CAAGGGGAGAGTGGGCACGACATAAAAATT
ValGluAspSerIleIleArgThrGlyPhe  GlnGlyGluSerGlyHisAspIleLysIle
                           410                              420

CTGGACGTTAATAAGTCCAAGACTCATATT  TCCGTAAATGGTCGGAAAATAAGGATGCGT
LeuAspValAsnLysSerLysThrHisIle  SerValAsnGlyArgLysIleArgMetArg
                           450                              460

AATGGTGTGCATGCGAATCTTCACGTGGCA  TTTCACAGAAGCAGCTCGGAGAAAATTCAT
AsnGlyValHisAlaAsnLeuHisValAla  PheHisArgSerSerSerGluLysIleHis
                           490                              500

ACCAAGGTTAATTCTAAGCTATCGCTATTT  TTTGAAATCAAAAGCTGAAAGGTAGTGGGG
ThrLysValAsnSerLysLeuSerLeuPhe  PheGluIleLysSerTer
                           530
```

FIG. 5c

```
  ↓   ↓↓↓ ↓ ↓
TCTCCGGGGCATAAAACGCAACCATTTCTT  CATGACGGGTATGCTGTCAGTTGGAACACT
SerProGlyHisLysThrGlnProPheLeu  HisAspGlyTyrAlaValSerTrpAsnThr
                           390                               400

ACTGCTGAAAATACCCCGCTTCCAATCGCG  GGTGTCCTACTACCGACTATTCCTGGAAAG
ThrAlaGluAsnThrProLeuProIleAla  GlyValLeuLeuProThrIleProGlyLys
                           430                               440

TGCAGAGCTATAGACGGTGATGTAACTTTT  TGTCGCCCTAAATCTCCTGTTTATGTTGGT
CysArgAlaIleAspGlyAspValThrPhe  CysArgProLysSerProValTyrValGly
                           470                               480

TCTAATGAAATTTCGTCGGATTCCATAGGC  GTTCTTGGGTACCAGAAAACAGTAGATCAC
SerAsnGluIleSerSerAspSerIleGly  ValLeuGlyTyrGlnLysThrValAspHis
                           510                               520

TCGTGTGCCGG
```

FIG. 5d

DIPHTHERIA TOXIN RECEPTOR-BINDING REGION

This is a continuation of application Ser. No. 08/119,316, filed Sep. 9, 1993 now abandoned; which in turn is a continuation of application Ser. No. 07/881,394, filed May 6, 1992, now abandoned.

This invention was made with Government support under GM31299 and GM39558 awarded by the National Institute of Health, and under AI-22021 and AI-22848 awarded by the National Institute of Arthritis and Infectious Diseases. The government has certain rights in the invention.

BACKGROUND OF THE INVENTION

This invention relates to diphtheria toxin.

Diphtheria was a leading cause of death among children until mass immunization against diphtheria toxin reached the general public in the late 1920's. Current methods of controlling diphtheria include therapeutic administration of antibodies as antitoxins that are specifically directed against the disease itself, and mass immunization with formaldehyde-inactivated diphtheria toxin, referred to as toxoid. Although the latter is capable of inducing specific antitoxin antibody formation, preparations of the toxoid contain a high proportion of contaminants (30%–40%) that can be responsible for occasional adverse effects of vaccination. (Rappouli, in *New Generations Vaccines*, ed. Woodrow, L. Dekker publ. 1990. p. 251–268).

Diphtheria toxin is secreted as a single polypeptide chain of 535 residues from strains of *Corynebacterium diphtheriae* lysogenized by a bacteriophage carrying the tox gene (Greenfield, et al.,1983, *Proc Natl Acad Sci USA* 80:6853–6857). Mild trypsinization and reduction of diphtheria toxin in vitro generates two fragments, Fragment A (N-terminal ~21K) and Fragment B (C-terminal ~37K), as a result of cleavage at residue 190, 192, or 193 (Moskaug, et al., 1989, *Biol Chem* 264:15709–15713; Collier, et al., 1971, *Biol Chem*, 246:1496–1503). A similar proteolytic cleavage ('nicking') occurs in vivo before or soon after the toxin binds to a sensitive cell (Sandvig, et al., 1981, *J Biol Chem* 256:9068–9076).

The process by which diphtheria toxin intoxicates sensitive eukaryotic cells involves at least the following steps: (1) The binding domain of diphtheria toxin, a region at the C-terminal of Fragment B sometimes termed the "R region", binds to specific receptors on the surface of a sensitive cell. Receptors that bind to the R region are found on many different types of eukaryotic cells (Middlebrook, J. L., et al., 1977. *Can J Microbiol* 23:183–189.). (2) While bound to its receptor, the toxin molecule is internalized into an endocytic vesicle. (3) Either prior to internalization, or within the endocytic vesicle, the toxin molecule undergoes a proteolytic cleavage between Fragments A and B. (4) As the pH of the endocytic vesicle decreases to below 6, the toxin spontaneously inserts into the endosomal membrane, a process involving the translocation domain of the toxin, a domain located in the N-terminal region of Fragment B. (5) Once embedded in the membrane, the translocation domain of the toxin facilitates the delivery of Fragment A into the cytosol. (6) Fragment A in the cytoplasm catalyzes the transfer of the ADP-ribosyl group of NAD$^+$ to elongation factor 2 (EF-2), a factor crucial for protein synthesis in eukaryotes. This inactivates EF-2, stopping protein synthesis and killing the target cell. Introduction of a single molecule of Fragment A into the cytoplasm of a cell is sufficient to kill the cell (Yamaizumi, et al., 1978, *Cell* 15:245–250).

SUMMARY OF THE INVENTION

In general, the invention involves the use of the R region of diphtheria toxin as an immunogen in a vaccine against diphtheria. Preparations of the diphtheria toxin R region can also be used as therapeutic agents against the progress of diphtheria. Applicants have determined, by the use of X-ray crystallography, the boundaries of the R region as a distinct domain within the diphtheria toxin polypeptide, as well as a large loop, constituting residues 496–512 (SEQ ID NO: 1) (the "receptor binding loop") which represents a likely candidate for the receptor binding region. With this knowledge, the R region, or the receptor binding loop, or a polypeptide that begins at the N-terminal boundary of the R region and extends to the C-terminal boundary of the receptor binding loop, or a polypeptide that begins at the N-terminal boundary of the receptor binding loop and extends to the C-terminus of diphtheria toxin can now be produced as separate polypeptide entities that have superior stability, safety, and immunogenic characteristics, or as synthetic peptides with associated ease of preparation and administration.

The invention features a polypeptide, or a substantially pure preparation of a polypeptide, consisting essentially of a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535,
or s) amino acids 496–524, all of FIG. 5 (SEQ ID NO:1). Each of these polypeptides is hereafter referred to in this document as "the R region polypeptide". By substantially pure is meant that at least 50% (by weight) of the protein present in the preparation is the R region polypeptide. In preferred embodiments, at least 75%, more preferably at least 90%, and most preferably at least 99% (by weight) of the protein present in the preparation is the R region polypeptide.

The invention also includes a DNA encoding the R region polypeptide, wherein the DNA does not encode an amino acid sequence corresponding to amino acids 291 to 378 of FIG. 5 (SEQ ID NO:1) immediately adjacent to the amino terminal end of the R region polypeptide; a vector including that DNA sequence, preferably a vector wherein the DNA sequence encoding the R region polypeptide is under the control of a heterologous promoter, or more preferably a vector wherein the expressed amino acids are linked to a signal sequence; a cell, or a homogeneous population of cells, containing the DNA encoding the R region polypeptide. The cell is preferably capable of expressing the R region polypeptide, and most preferably is a carrier vaccine microbe. A "carrier vaccine microbe", as used herein, is either a naturally avirulent live microorganism, or a live microorganism with either low or attenuated virulence, that expresses an immunogen. Examples of attenuated viral or bacterial vaccine strains that serve as carrier vaccine microbes are listed below. By "heterologous promoter" is meant a promoter region that is not identical to the naturally-occuring promoter region corresponding to the given gene. The promoter region is a segment of DNA 5' to the transcription start site of a gene, to which RNA polymerase binds before initiating transcription of the gene.

The invention also features an essentially pure preparation of nucleic acid that includes a sequence encoding the R region polypeptide, wherein the nucleic acid does not encode an amino acid sequence corresponding to amino acids 291 to 378 of FIG. 5 (SEQ ID NO:1) immediately adjacent to the amino terminal end of the R region polypeptide. By "an essentially pure preparation of nucleic acid" is meant a preparation containing the nucleic acid of the invention, and which is substantially free of other nucleic acid molecules with which a DNA encoding diphtheria toxin is naturally associated in *Corynebacterium diphtheriae*. The R region polypeptide is preferably prepared by chemical synthesis (i.e., by either classical or automated methods of organic chemistry), or by biological synthesis (i.e., by producing the polypeptide from a set of genetic instructions). The cells of the invention can be used in a method involving providing the cell, growing the cell in a medium to form a population of cells that express the R region polypeptide, and obtaining the R region polypeptide from the population of cells or the medium.

The invention also features a therapeutic composition that includes the R region polypeptide and a pharmaceutically acceptable carrier. The therapeutic composition can be used, for example, in a method of treating diphtheria in a human patient, including the steps of identifying a patient suspected of having diphtheria, and administering a therapeutically-effective amount of the therapeutic composition to the patient. By "pharmaceutically acceptable carrier" is meant an inert substance that forms a vehicle for a therapeutic composition.

In another embodiment, the invention features a method of preventing intoxication of cells by diphtheria toxin involving contacting the cells with an intoxication-preventing amount of the R region polypeptide.

A human patient can be immunized against diphtheria toxin, by administering to the patient an immunogenically effective amount of one of the following vaccines of the invention: 1) a vaccine that includes the R region polypeptide of the invention, but does not include an amino acid sequence corresponding to amino acids 291 to 378 of FIG. 5 (SEQ ID NO:1) immediately adjacent to the amino terminal end of the R region polypeptide; 2) a vaccine that includes an attenuated viral vector containing DNA encoding the R region polypeptide [an "attenuated viral vector", as used herein, refers to a virus that provides replication functions for an attached gene of interest, and that is avirulent, has low virulence, or whose virulence in humans is reduced relative to a naturally occurring virus of the same type]; 3) a vaccine that includes an attenuated bacterium containing DNA encoding the R region polypeptide [an "attenuated bacterium", as used herein, refers to a bacterium whose viability is reduced relative to a naturally occurring bacterium of the same type]; or 4) a vaccine that includes a vector, which includes a DNA sequence encoding the R region polypeptide, wherein the DNA does not encode an amino acid sequence corresponding to amino acids 291 to 378 of FIG. 5 (SEQ ID NO:1) immediately adjacent to the amino terminal end of the R region polypeptide, preferably wherein the DNA sequence is under the transcriptional control of a heterologous promoter and/or the expressed amino acids are linked to a signal sequence. One, but not the only, method of administering a vaccine that includes a vector is by biolistic transfer, a method of delivery involving coating a microprojectile with DNA encoding an immunogen of interest, and injecting the coated microprojectile into cells of the recipient. The R region polypeptide is then expressed from the DNA to stimulate an immune response in the recipient (Tang, et al. 1992. *Nature* 356:152–154; hereby incorporated by reference). By incorporating immunogens that react with diphtheria toxin, the vaccines of the invention immunize against progression of the disease diphtheria, and against infection by the bacterium *Corynebacterium diphtheriae*.

In a related aspect, the invention features a fusion polypeptide consisting of the R region polypeptide linked by a peptide bond to an additional polypeptide, provided that the fusion polypeptide does not comprise a sequence corresponding to amino acids 291 to 378, preferably 310 to 378, more preferably 335 to 379, or most preferably 360 to 378 of FIG. 5 (SEQ ID NO: 1) immediately adjacent to the amino terminal end of the R region polypeptide. Preferably, the fusion polypeptide is included in a vaccine, which can be used to immunize a human patient against diphtheria toxin. The DNA encoding the fusion polypeptide can be incorporated into a cell, and preferably that cell (e.g. a carrier vaccine microbe) is then capable of expressing the fusion polypeptide. "Fusion polypeptide", as used herein, refers to a protein molecule produced by expression of a hybrid DNA in which a DNA encoding the R region polypeptide is linked by means of genetic engineering to a second DNA encoding a second polypeptide sequence.

In a similar aspect, the invention features the R region polypeptide attached to a chemical group. A therapeutic composition can include the R region polypeptide attached to a chemical group and a pharmaceutically acceptable carrier. A method of treating diphtheria in a human patient involves identifying a patient suspected of having diphtheria, and administering a therapeutically-effective amount of the composition containing the R region polypeptide attached to a chemical group to the patient. By "chemical group" is meant a molecule not normally associated with naturally occurring diphtheria toxin. Examples of suitable chemical groups can include, but are not limited to, polysaccharides from various pathogens, e.g., *Hemophilus influenzae, meningococci*, or *pneumococci*; or peptides corresponding to surface components or virulence factors of various bacterial or viral pathogens. A chemical group can serve as a carrier substance for the R region polypeptide. Conversely, the R region polypeptide can serve as a carrier substance for any of these chemical groups, or for other chemical groups (such as enzymes, or immunogens of other pathogens) not listed herein. A "carrier substance" is a substance that confers stability on, and/or aids the transport or immunogenicity of, an associated molecule.

In a final aspect, the R region polypeptide is combined with an adjuvant. The combined polypeptide and adjuvant can be used in a vaccine, and the vaccine used in a method to immunize a human patient against diphtheria toxin. Adjuvants can include, but are not limited to, any known type of adjuvant such as aluminum salts, bacterial endotoxins, bacillus Calmette-Guerin (BCG), liposomes, or Freund's adjuvant. An "adjuvant", as used herein, is a substance that is capable of increasing the immunogenicity of an antigen.

Applicants have defined the boundaries of the R region of diphtheria toxin, as well as the boundaries of loops within the R region that represent likely candidates for sequences involved in receptor binding, and have recognized the use of polypeptides based upon these portions of diphtheria toxin as safe and stable immunogens in a new vaccine against diphtheria toxin. By doing so, Applicants have made it possible to express the R region, or the sequence of one of these loops, as a separate entity. Immunizing with the R region polypeptide of the invention has certain advantages over immunizing with the whole diphtheria toxin polypeptide: for example, the patient is never exposed to the portion of the molecule bearing the toxic, enzymatic activity of the toxin (the Fragment A portion); there is no risk of reversion to an enzymatically active form; and since the patient is exposed to neither Fragment A nor the TM domain, subsequent use of either or both of these regions as a portion of an immunotoxin will not induce a secondary immune response. With the boundaries of the R region accurately defined by X-ray crystallographic analysis, an R region polypeptide of the invention can reproducibly assume its native, functional conformation.

Another advantage of this invention is that the R region polypeptide can be used therapeutically to bind to its receptor and thereby competitively prevent attachment of native diphtheria toxin to the receptor. Furthermore, as the R region polypeptide binds very efficiently to its receptor, which is found on a wide variety of cell types, the R region polypeptide would be a stable and efficient carrier molecule for drug delivery. In addition, the R region polypeptide can act as a stable carrier molecule for less stable immunogens, examples of which are listed herein.

Other features and advantages of the invention will be apparent from the following detailed description and from the claims.

DETAILED DESCRIPTION

The drawings will briefly be described.

Drawings

FIG. 1 is a diagrammatic representation of the X-ray crystallographic structure of the diphtheria toxin protein. a) Ribbon drawing of diphtheria toxin labelling each secondary structural segment. The first letter denotes the domain: C for catalytic, T for transmembrane, and R for receptor-binding domains. The second letter denotes the secondary structure class: H for helix, B for β strand, L for loop. The third symbol is the sequential number of each secondary segment from the N-terminus of each domain. The residue numbers in each segment are as follows: CH1:2–7, CB1:11–14, CB2:16–24, CH2:28–34, CB3:52–57, CH3:58–66, CB4:76–86, CB5:88–96, CH4:99–106, CH5:120–126, CB6:130–136, CB7:147–152, CB8:159–166, CH6:168–173, CH7:176–186; TH1:205–221, TH2:225–231, TH3:238–257, TH4:258–269, TH5:274–288, TH6:297–307, TH7:310–315, TH8:326–346, TH9:356–378; RB1:386–390, RB2:393–399, RB3:412–424, RB4:428–438, RB5:447–453, RB6:455–465, RB7:467–480, RB8:483–495, RB9:513–520, and RB10:525–534. b) Stereo diagram of the Cα skeleton of diphtheria toxin from the same viewpoint as that of panel a. An ApUp molecule occupies the active site of diphtheria toxin. c) Stereo pairs of electron density maps calculated at 2.5 Å from $(2F_{ob}-F_c)$ and the refined model phases. Maps are super-imposed on the corresponding region of the refined model. d) The diphtheria toxin dimer observed within the Form4 crystal. The two monomers are related by a crystallographic 2-fold rotation axis, which is vertical. The molecule at the left (in thick line) has the same orientation as that in panel a.

Figure 2:

FIG. 2. Stereo pair of Cα skeleton of the C Domain. The entrance to the active site is at the lower right. The four loops, CL1 to CL4, are shown by a thickened line. Notice that they form a hinge which can permit the C domain to form a more elongated structure.

FIG. 3. Stereo pair of the Cα skeleton of the T domain, with the direction of view from the right side of diphtheria toxin in FIG. 1. Helix TH1 lies in back, starting at residue 205. Helix TH2 runs to the left at the bottom, followed by a turn and helix TH3 running to the right. In front center is TH5 (running to the left) and above it are helices TH6 and TH7. Behind these pairs of antiparallel helices is another pair of antiparallel helices, TH8 and TH9, with TH9 running upwards and ending at residue 378. a) Asp and Glu side chains are shown. Notice the tips of two helix layers, TL3 and TL5 contain a total of six acidic groups (on the left). b) Lys, Arg and His side chains are shown. Notice the positive charge asymmetry, with all charges at the bottom and back of the domain, with the exception of $Lys_{299}$ near the loop TL3 between TH5 and TH6.

Figure 4:
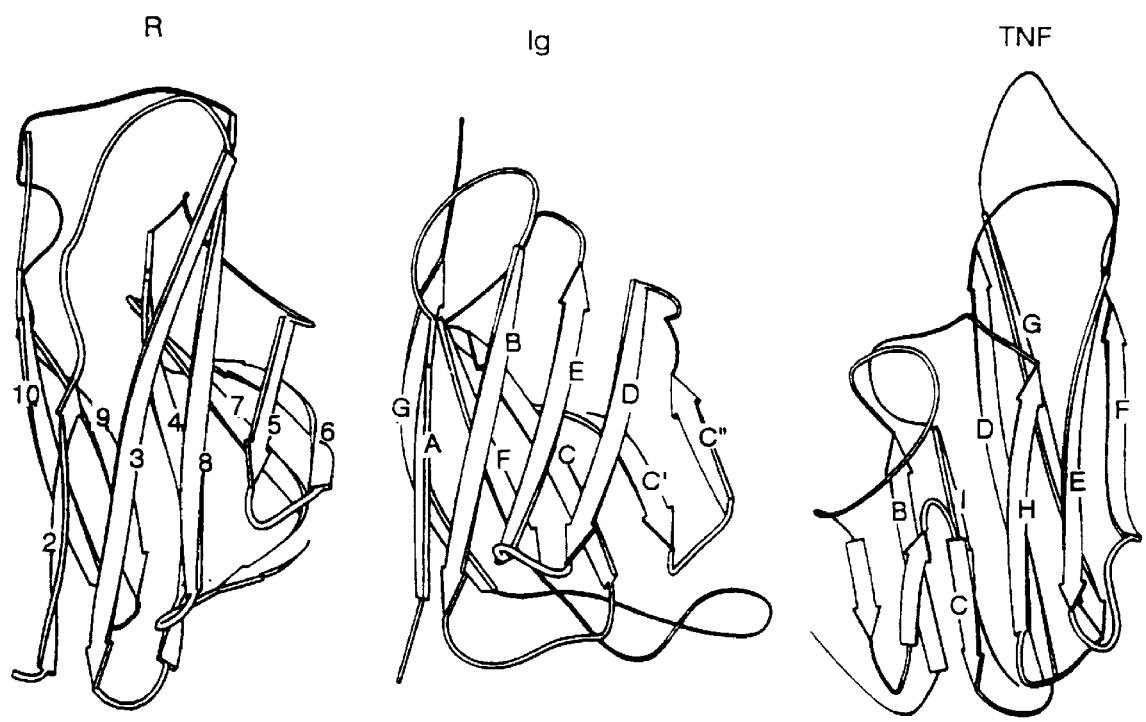

FIG. 4. The topology of the R domain of diphtheria toxin (left) is compared to that of an Ig variable domain (center) (Marquart, et al., 1980, *J Mol Biol* 141:369) and to tumor necrosis factor (TNF, right) (Eck, et al., 1989, *J Biol Chem*, 264:17595). R domain is viewed in the direction from the back side of diphtheria toxin in FIG. 1. Numbers from 2 to 10 of the R domain represent the strands RB2 through RB10 of diphtheria toxin. Notice that strands 2, 3, 4, 8, 9, and 10 of the R domain correspond well to strands A, B, C, E, F, and G of the Ig variable domain. Also strands 3, 4, 5, 6, 7, 8, and 9 correspond well to strands C, D, E, F, G, H, and I of TNF, a classical jellyroll (Jones, et al., 1989, *Nature* 338:225–228).

Figure 5:
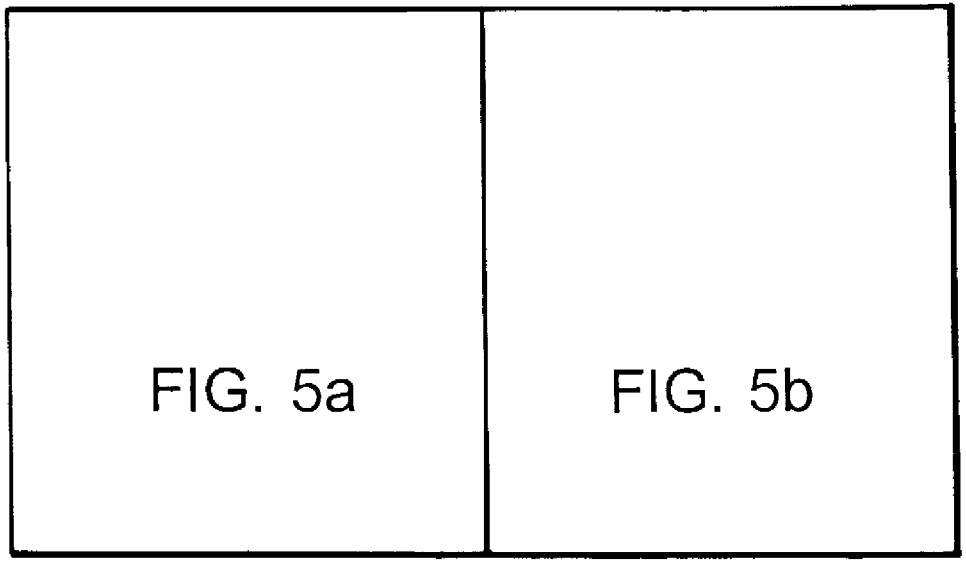
Figure 5:
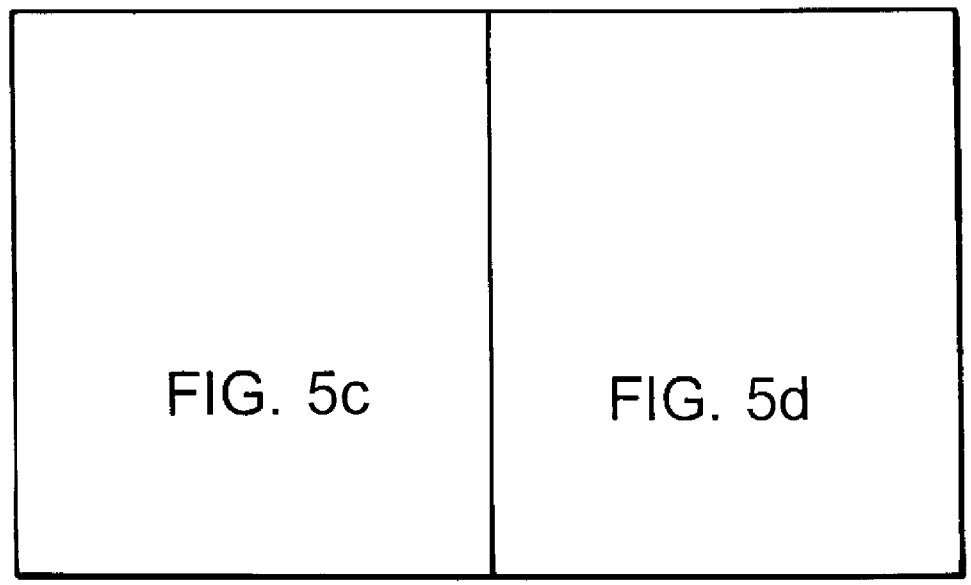

FIG. 5 is a diagrammatic representation of the wildtype nucleotide and corresponding amino acid sequences of mature diphtheria toxin (SEQ ID NO: 1), with the amino termini of the various polypeptides of the invention indicated by arrows. Amino acid Gly 1 represents the first amino acid of the mature wildtype polypeptide, after the N-terminal signal sequence is removed.

Applicants' objective is to produce a diphtheria toxiod that is safe to introduce into a human patient, even when the vaccine is in the form of a live, attenuated virus or bacterium genetically engineered to express the toxoid in the vaccine. Such a live vaccine leaves the DNA encoding the toxoid susceptible to mutation as the vaccine strain reproduces itself in vivo. Whenever the vaccine DNA includes a copy of an inactive form of the active Fragment A of diphtheria toxin, however mutated to destroy its cell-killing ability, there is a risk that those mutations can be reversed or silenced by subsequent spontaneous mutations in vivo. Only where the vaccine does not include a Fragment A at all does this risk go to zero.

The diphtheria toxin is composed of three structural domains. Of the three, the R region serves a receptor recognition function by binding the molecule to receptor bearing cells. This R region, produced as an entity separate from the remainder of the diphtheria toxin molecule, would serve as a good toxoid in a vaccine against diphtheria. The R region defined by Applicants is a stable domain and is the primary antigenic determinant of whole diphtheria toxin protein. This idea is based on the crystallographic structure of diphtheria toxin, together with the results of Rolf, et al., showing that a carboxyl-terminal peptide of diphtheria toxin (HA6DT) inhibited toxin activity by competitively binding to toxin-specific receptors. The peptide, comprised of amino acids 482–535 (MW 5982 Da), was prepared by hydroxylamine treatment of diphtheria toxin (Rolf, et al., 1991, FASEB 75th Annual Meeting, 5:A821, hereby incorporated by reference). However, such a fragment is unlikely to possess both the antigenic specificity and the in vivo stability that would make it a good candidate for a vaccine. The R region polypeptide defined herein possesses a stable tertiary structure that allows it to induce efficient formation of antibodies which will target intact diphtheria toxin. In addition, the R region polypeptide of the invention is relatively stable to proteolytic degradation in vivo.

Structure Determination-Methods

Data defining the R region boundary are provided by the X-ray crystallographic structure (FIG. 1). The structure is based on analyses of Form1, Form3, and Form4 crystals. Form1 crystals of diphtheria toxin complexed with adenylyl-3',5'-uridine monophosphate (ApUp) belong to triclinic space group P1 with unit cell dimensions of a=70.4 Å, b=70.6 Å, c=65.4 Å, α=94.9°, β=91.0°, and γ=99.6° with two chains per asymmetric unit. This dimeric asymmetric unit is consistent with the discovery, after our initial report of crystallization (Collier, et al., 1982, *J Biol Chem* 257:5283–5285), that the crystals were of a dimeric form of diphtheria toxin sometimes found in crude or purified preparations of the protein. Dimeric diphtheria toxin itself is not toxic, presumably because it does not bind to receptors, but it slowly dissociates to fully toxic monomers (Carroll, et al., 1986, *Biochemistry* 25:2485–2430). The dimer can represent a conformationally altered form of the biologically active monomeric toxin. Irreproducible crystallization conditions for obtaining Form1 crystals hampered crystallographic studies of structure determination until three new crystal forms were obtained (Fujii, et al., 1991, *J Mol Biol* 222:861–864). Form3 and Form4 belong to monoclinic space group C2 with unit cell dimensions for Form3 of a=107.3 Å, b=91.7 Å, c=66.3 Å, and β=94.7°, and for Form4 of a=108.3 Å, b=92.3 Å, c=66.1 Å, and β=90.4°. In both of these forms there is one diphtheria toxin chain per asymmetric unit and pairs of diphtheria toxin chains are related by a 2-fold rotation axis.

The initial model was based on the structure determination of Form4 crystals at 3.0 Å resolution, using the multiple isomorphous replacement (MIR) method followed by solvent flattening (Wang, 1985, *Methods of Enzymol* 115:90–112). With the initial model, the structures of Form1 and Form3 were readily solved by molecular replacement (Brünger, 1991, *Acta Cryst* A47:195–204; Rossmann, et al., 1962, *Acta Cryst* 15:24–31). Single isomorphous replacement (SIR) phases were also obtained for Form3. Native data were then collected to 2.5 Å resolution, and the model was rebuilt into 2.5 Å maps with Form3 (SIR) and Form4 (MIR) after the phases had been extended and modified by the method of Zhang and Main (Zhang, et al., 1991, *Acta Cryst* A46:377–381). This was followed by real-space density averaging between two forms. Sequence fitting was difficult in the ~120 C-terminal residues (part of receptor-binding or R domain) where the most ambiguous regions were near residues 408 and 510. Some of the useful markers in the density maps were $W_{50}$, $W_{153}$, $W_{281}$, $W_{398}$, a 5-residue segment of $M_{178}$, $Y_{179}$, $E_{180}$, $Y_{181}$, $M_{182}$, a 4-residue cluster of $F_{355}$, $Y_{358}$, $H_{372}$, $Y_{375}$, a cluster of $Y_{514}$, $F_{530}$, $F_{531}$, with big side chains near the C-terminus (FIG. 1c), and two disulfide bonds between $C_{186}$, and $C_{201}$, and $C_{461}$, and $C_{471}$. An initial improper fitting in the R domain was detected by profile window plots (Lüthy, et al., 1992, *Nature* 356:83–85) and then corrected. Iterative cycles of refinement were carried out independently at 2.5 Å for each set of data. The atomic model for each form is essentially identical except for crystal packing. Details of phase modification and refinement will be described elsewhere. Assessment of the accuracy of the model rests on the fit of the model to the MIR and density-modified maps, crystallographic R-factors, real-space R-factors (Jones, et al., 1991, *Acta Cryst* A47:110–119), the free R-value (Brünger, 1992, *Nature* 355:472–475), which is only 4% higher than the crystallographic R factor, and profile window plots (Lüthy, et al., 1992, *Nature* 356:83–85). At the present stage of refinement, the agreement of the atomic models to crystallographic data is characterized by R factors of 21.1, 21.6, and 21.9%, respectively, for Form1, Form3, and Form4 for all observed data having $F_{ob}$ greater than 1 $\sigma(F_{ob})$ between 6 and 2.5 Å resolution.

The final model consists of 4137 non-hydrogen atoms with individual isotropic temperature factors. The model also includes ApUp in the active site cleft of the catalytic (C) domain, but no solvent atoms. There are poorly-defined regions in the electron density maps where main chain densities for residues 170–172, 190–195, 389–390, and 500–503, are not well defined. Residues 190–195 are part of the protease-sensitive region of the first disulfide loop, where nicking occurs; this region can be intrinsically flexible. So can be the loop between the transmembrane (T) and R domains, which includes residues 389–390.

Table 1 summarizes aspects of data collection, phase determination and refinement.

Explanation of Table 1

Crystal Forms 1, 3, and 4 were used for the current study (Fujii, et al., 1991, *J Mol Biol*, 222:861–864).

Diffraction data were collected on a Rigaku AFC-6 diffractometer operating at 8.5 kW, equipped with a two-panel area detector of Xuong-Hamlin design (San Diego Multiwire Systems, San Diego, Calif.). Images were recorded as 0.1° oscillation frames, integrated and merged into batches of 50 frames (5°). Integrated intensities were scaled and merged by FOURIER scaling method (Weissman, L. 1979. Ph.D thesis, Univ. of California, Los Angeles). Form4 native and derivative data were later collected to 2.5Å with a RAXIS imaging plate system.

Heavy atom derivatives. KOS, $K_2O_sO_4$, soaked for 3 days at the saturated concentration in artificial mother liquor (12% PEG 8000, 0.43M NaCl, 43 mM Tris-HCl, pH 7.8); CNP, 4-chloro-2-nitro-mercury phenol, soaked for 5 days at the saturated concentration in artificial mother liquor; KNP, 1 to 1 mixture of KOS and CNP; CAP, trans-dichlorodiamine Platinum (II), soaked for 3 days at 2 mg/ml in artificial mother liquor; KAP, 1 to 1 mixture of KOS and CAP; GCL, $HgCl_2$, soaked for 3 days at 2 mg/ml in artificial mother liquor.

Heavy atom parameters were refined and MIR phases calculated using the program HEAVY (Terwilliger, et al., 1987, *Acta Cryst*, A431–5). We initially obtained the Os derivative for Form3 crystals. From electron density maps based on the single isomorphous replacement (SIR) phases after solvent flattening at 3.5 Å resolution, the shape of the molecule was interpreted to have three domains.

TABLE 1

| NATIVE DATA | | | OVERALL($R\dagger_{scale}$) | 10–4.0 | 4.0–3.5 | 3.5–3.0 | 3.0–2.5 Å |
|---|---|---|---|---|---|---|---|
| Form4 | | Total | 36758(11.9) | 26897 | 4977 | 4884 | |
| | | Unique (% complete) | 10875(83) | 5190(99) | 2414(92) | 3271(63) | |
| Form4(new) | | Total | 35897(6.1) | | | | |
| | | Unique (% complete) | 18665(84) | 5195(99) | 2673(98) | 4268(82) | 6529(72) |
| Form3 | | Total | 61009(7.6) | 21984 | 15368 | 10573 | 13084 |
| | | Unique (% complete) | 19912(90) | 5231(100) | 2682(98) | 4603(88) | 7396(82) |
| Form1 | | Total | 66464(7.5) | 22245 | 21118 | 15277 | 7824 |
| | | Unique (% complete) | 25854(68) | 6523(96) | 7665(92) | 7102(76) | 4574(35) |
| DERIVATIVES | | | OVERALL | 10–4.6 | 4.6–3.6 | 3.6–3.0 | 3.0–2.8 Å |
| Form4 | | | | | | | |
| KOS | | Unique ($R\dagger_{scale}$) | 11765(9.16) | | | | |
| | | $R\ddagger_c(fh/e\mathcal{f})$ | 0.66(1.23) | 0.66(1.29) | 6.62(1.18) | 0.75(1.28) | 0.80(1.06) |
| CNP | | Unique ($R^{\dagger scale}$) | 12255(12.0) | | | | |
| | | $R\ddagger_c(fh/e\mathcal{f})$ | 0.70(1.06) | 0.68(1.33) | 0.72(0.93) | 0.72(0.97) | 0.66(1.11) |
| KNP | | Unique ($R^{\dagger scale}$) | 8164(8.32) | | | | |
| | | $R\ddagger_c(fh/e\mathcal{f})$ | 0.71(1.00) | 0.72(0.87) | 0.67(1.18) | 0.75(1.33) | |
| CAP | | Unique ($R^{\dagger scale}$) | 7552(15.3) | | | | |
| | | $R\ddagger_c(fh/e\mathcal{f})$ | 0.71(1.28) | 0.70(1.54) | 0.72(1.12) | 0.88(1.20) | |
| KAP | | Unique ($R^{\dagger scale}$) | 10152(12.26) | | | | |
| | | $R\ddagger_c(fh/e\mathcal{f})$ | 0.81(1.26) | 0.81(1.43) | 0.71(1.19) | 0.75(0.89) | |
| GCL | | Unique ($R^{\dagger scale}$) | 6595(11.90) | | | | |
| | | $R\ddagger_c(fh/e\mathcal{f})$ | 0.70(1.10) | 0.69(1.13) | 0.66(1.09) | 0.50(1.05) | |
| Form3 | | | | | | | |
| KOS | | Unique ($R^{\dagger scale}$) | 11435(13.57) | | | | |
| | | $R\ddagger_c(fh/e\mathcal{f})$ | 0.54(1.10) | 0.56(1.32) | 0.60(0.74) | | |
| | | Refinement | Form1 | Form3 | Form4 | | |
| | | R factor ¶ (6–2.5Å) | 0.211 | 0.216 | 0.219 | | |
| | | r.m.s. bond (Å) | 0.021 | 0.021 | 0.021 | | |
| | | r.m.s. angle (°) | 4.54 | 4.40 | 4.48 | | |
| | | r.m.s. dihedral (°) | 26.4 | 25.9 | 26.1 | | |

Footnote to Table 1.
$R\dagger_{scale} = \Sigma(|I_i - I_j|)/\Sigma(I_{av})$ where $I_i$ and $I_j$ are the ith and jth measurements of the equivalent reflections (Weissman, L., 1979, Ph.D. thesis, Univ. California, Los Angeles).
‡Rc is Cullis R factor for centric reflections. $\mathcal{f}$fh/e is the phasing power, fh, the mean amplitude of heavy atom structure factors divided by e, the r.m.s. lack-of-closure error.
¶R factor = $\Sigma(|F_{ob} - F_c|)/\Sigma(F_{ob})$ where $F_{ob}$ and $F_c$ are the structure factors observed and calculated from the model, respectively. The R-factors for all forms increased by about 1.9% when a single temperature factor was used for all atoms.

However, secondary structures were not easily interpretable and the course of the polypeptide chain was difficult to determine. A search for additional heavy atom derivatives was hampered by the lack of good quality crystals of Form3. We, therefore, shifted our efforts to Form4 crystals. MIR phases for Form4 were obtained form six heavy atom derivatives using isomorphous differences and anomalous differences. The Os and Pt derivatives were solved by isomorphous difference Patterson functions, and the Hg derivative by a difference Fourier synthesis. Os derivatives of Form4 and Form3 have the same single site binding.

Solvent flattening. Initial electron density maps of Form4 were calculated at 3.0 Å resolution, with phases modified using an iterative solvent flattening procedure (Wang, 1985, *Methods in Enzymol*, 115:90–112) including phases extended to 3.0 Å from 3.2 Å by the Wang phase extension algorithm (Wang, 1985, *Methods in Enzymol*, 115:90–112). A solvent volume of 45% was used to ensure that all protein density was included in the protein mask, somewhat smaller than the 57% estimated from the molecular weight. From these maps, all secondary structures were identified and an initial model was built using a polyalanine chain.

Model building was expedited with the program FRODO (Jones, 1985, *Methods in Enzymol*, 115:157–171) and the fragment-fitting routines of the program O (Jones, et al., 1991, *Acta Cryst*, A47). Starting with α carbon coordinates that were manually built, main chain atoms were added using the database of 34 well-refined protein structures. Then side chains were added using the rotamer database (Ponder, et al., 1987, *J Mol Biol*, 193:775–791).

Refinement. This initial model was adjusted by visual inspection of density maps before it was refined by the simulated annealing protocol of the program XPLOR (Brüger, 1990, *Acta Cryst*, A46:585–593). The relative orientations of diphtheria toxin in Forms 1, 3 and 4 were determined by a Patterson-space rotation and translation search of the refined Form4 model against Form1 and Form3 data. Two top solutions (9σ) for Form1 data correspond to two diphtheria toxin chains related by a noncrystallographic symmetry in asymmetric unit. The transformation from Form4 to Form 1 is essentially a change of coordinate system from C2 to P1, where the crystallographic rotation axis of C2 becomes a noncrystallographic rotation symmetry axis of P1 that is nearly parallel with (110) axis of P1. One top solution (7σ) for Form3 corresponds to a rotation of less than 0.5° in any direction. The transformation from Form4 to Form3 is essentially a 5 Å translation along the a axis. This result is consistent with the observation that the average absolute difference of the amplitudes of structure factors of 0kl reflections between Form3 and Form4 are 15%, while those differences between hk0 or h0L are almost random (R=48%). Also, when the model was superimposed on the solvent-flattened electron density maps of Form3 based on the SIR phases, most of the secondary structures were recognized with the model as a guide. Real-space averaging of densities between Form4 and Form3 with MIR and SIR phases at 3.0 Å improved the density maps at this stage. Subsequently, experimental phases were extended to 2.5 Å by the algorithm based on solvent flattening, histogram matching, and Sayre's equation (Zhong and Main, 1991, *Acta Cryst*, A46:377–381) for Form3 and Form4. Form3 maps at 2.5 Å were again skewed and averaged with Form4 maps. These were the most interpretable maps. Refinement of the atomic model was carried out independently for Form1, Form3, and Form4 with all observed data having $F_{ob}$ greater than 1 $\sigma(F_{ob})$ between 6 and 2.5 Å.

Structure of Diphtheria Toxin-Results

Diphtheria toxin consists of three abutting domains that are connected by interdomain linkers. The N-terminal C domain, middle T domain, and C-terminal R domain consist of residues 1–193, 205–378, and 386–535, respectively. Schematically, diphtheria toxin is Y-shaped with the base formed by the T domain, one arm of the Y formed by the C domain, and the other arm formed by the R domain. The Y is about 90 Å high, 50 Å across the top of the Y, but only 30 Å thick (FIG. 1).

Each of the three domains has a distinctive fold. The C domain is a mixed structure of eight β strands (CB1–CB8) and seven α-helices (CH-1-CH7). These eight β strands form two β sheets of 3 and 5 strands each. The β sheets form a core that is surrounded by 7 short helices. The overall folding of the C domain is similar to that of *Pseudomonas aeruginosa* exotoxin A (ETA) especially near the active site (Allured, et al., 1986, *Proc Natl Acad Sci USA* 83:1320–1324), a result that had been foreshadowed by a weak similarity in amino acid sequences (Caroll, et al., 1988, *Mol Microbiol* 2:293–296; Brandhuber, et al., 1988, *Proteins* 3:146–154). Sixma et al. (Sixma, et al., 1991, *Nature* 351:371–377) recently demonstrated that the folding of the active site region of *E. coli* heat labile enterotoxin also closely resembles that of ETA. The T domain contains nine helices (TH1–TH9) that are folded into three helix layers, each of which is formed by two or more antiparallel helices. A similar feature was observed in the structure of the channel-forming domain of colicin A (Parker, et al., 1989, *Nature* 337:93–96). The R domain contains ten β strands (RB1–RB10), nine of which (RB2–RB10) build two β sheets. These two β sheets form a β sandwich with a topology similar to a jellyroll fold (Richardson, 1981, *Adv Protein Chem* 34:167–339). The three-domain organization of diphtheria toxin is shared by two other bacterial toxins: ETA and δ-endotoxin from *Bacillus thuringiensis* (Li, et al., 1991, *Nature* 353:815–821). The catalytic domains of diphtheria toxin and ETA are the closest among all these domains in their structures and functions.

Catalytic domain

We view the C domain as being formed from the two β sheet subdomains, which subtend the active site cleft (FIG. 2). These β sheets are oriented roughly perpendicular to each other and form the core of the domain. One subdomain consists of β strands CB2, CB4, and CB8, surrounded by α-helices, CH2, CH3, CH6, and CH7. The other subdomain consists of β strands CB1, CB3, CB5, CB6, and CB7 surrounded by helices, CH1, CH4, and CH5. The two subdomains are connected by extended loops, CL1 through CL4, which link the two subdomains. These four loops appear to endow the potential for flexibility or even extension to a longer and narrower shape. Conceivably the C domain can assume this partially unfolded structure during membrane translocation.

The active site cleft of the C domain, identified by the binding of the dinucleotide ApUp, is formed primarily by β strands, CB2, CB3, CH3, CB7 and the loop, CL2, and is also bounded by β strand RB6 of the R domain. Located within the active site cleft are the following residues: $Glu_{148}$ which is believed to play a key role in catalysis (Carroll, et al., 1984, *Acad Sci USA* 81:3307–3311), $His_{21}$ (Papini, et al., 1989, *J Biol Chem* 264:12685–12388) and $Tyr_{65}$ (Papini, et al., 1991, *J Biol Chem*, 266:2494–2498), both of which have been implicated in NAD$^+$ binding, and various other residues suggested to be at or near the active site ($Gly_{52}$ (Carroll, et al., 1984, *Proc Natl Acad Sci USA*, 81:3307–3311; Giannini, et al., 1984, *Nuc Acid Res*, 12:4063–4069), $Trp_{50}$ (Collins, et al., 1985, *Biochim Biophys Acta* 828:138–143), $Lys_{39}$ (Zhao, et al., 1988, *Biochemistry*, 27:3398–3403), and $Lys_{474}$ (Proia, 1980, *J Biol Chem*, 255:12025–12033)). Least squares superposition of the a carbon coordinates of the C domains of diphtheria toxin and ETA yields an r.m.s. difference of 1.44 Å between 85 residues (16–33, 34–38, 49–66, 75–90, 91–96, 131–136, 147–164 of diphtheria toxin and 437–452, 454–458, 465–482, 493–508, 511–516, 540–545, 552–569 of ETA).

The approximate position of the substrate NAD$^+$ in the active site can be inferred, because the dinucleotide, ApUp, binds competitively with NAD$^+$. The high affinity of ApUp (~0.3 nM as compared with ~8–16 μM for NAD$^+$ (Carroll, et al., 1986, *Biochemistry*, 25:2425–2430)) can be a consequence of multiple contacts with the C domain and of salt bridges between the 3'-terminal phosphate of ApUp and the side chains of $Thr_{42}$ and $Arg_{458}$, the latter of which is a residue of the R domain. Although the structure of bound ApUp resembles that of NAD$^+$, there are enough differences between the covalent structures of NAD$^+$ and ApUp to make difficult the prediction of the conformation of NAD$^+$ in the cleft. However, assuming that the adenine phosphate portion of NAD$^+$ binds in the same conformation as that of ApUp, we find that the nicotinamide ring will be positioned close to the site of the uridine ring. This places the nicotinamide ring adjacent to side chains of $His_{21}$, $Tyr_{65}$, and $Glum_{148}$.

Domain junctions.

Figure 1A:
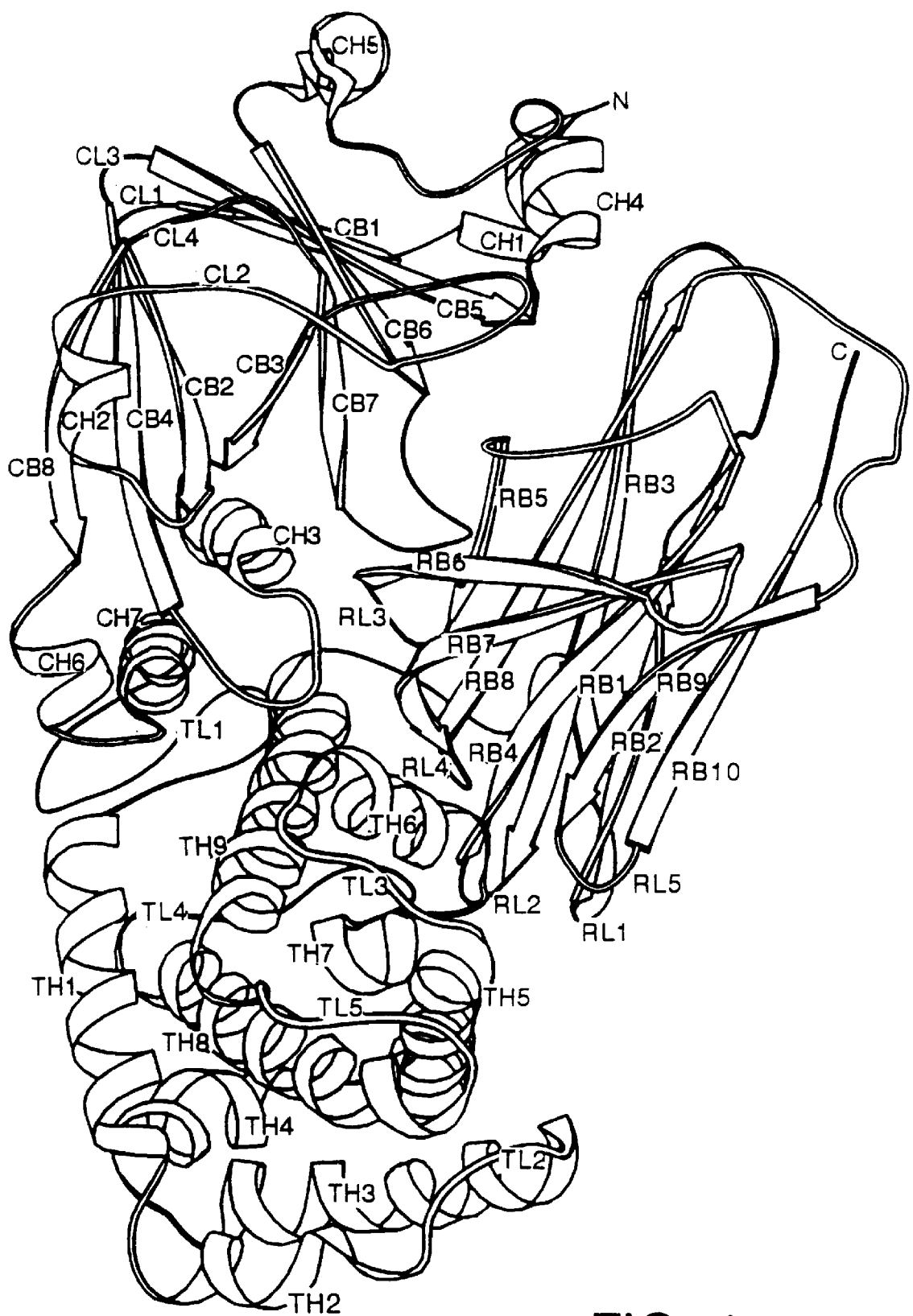

One of the two intramolecular disulfide bonds of diphtheria toxin bridges a handle-like loop TL1 on the molecular surface (FIG. 1a). This 14 residue loop (187–200) connects Fragment A to Fragment B; it is rich in Arg and known to be easily nicked by proteases (Moskaug, et al., 1989, *J Biol Chem* 264:15709–15713; Collier, et al., 1971, *J Biol Chem* 246:1496–1503). Once this loop is nicked, Fragment A and Fragment B are covalently linked only by the disulfide bond. There is evidence that nicking plays a role in the cytotoxic action of diphtheria toxin (Sandvig, et al., 1981, *J Biol Chem* 256:9068–9076), and it is generally believed that nicked diphtheria toxin separates into free Fragment A and Fragment B when this disulfide bond is exposed to the reducing environment of the endosome during membrane translocation of the toxin. The second disulfide bond makes a 9 residue loop between residues 461 and 471 within Fragment B. Residues near this loop (456,458,460,472,474) are also rich in positive charges and face the active site cleft, probably forming the so-called phosphate-binding "P-site" (Lory, et al., 1980, *Proc Natl Acad Sci USA* 77:267–271).

Figure 1B:
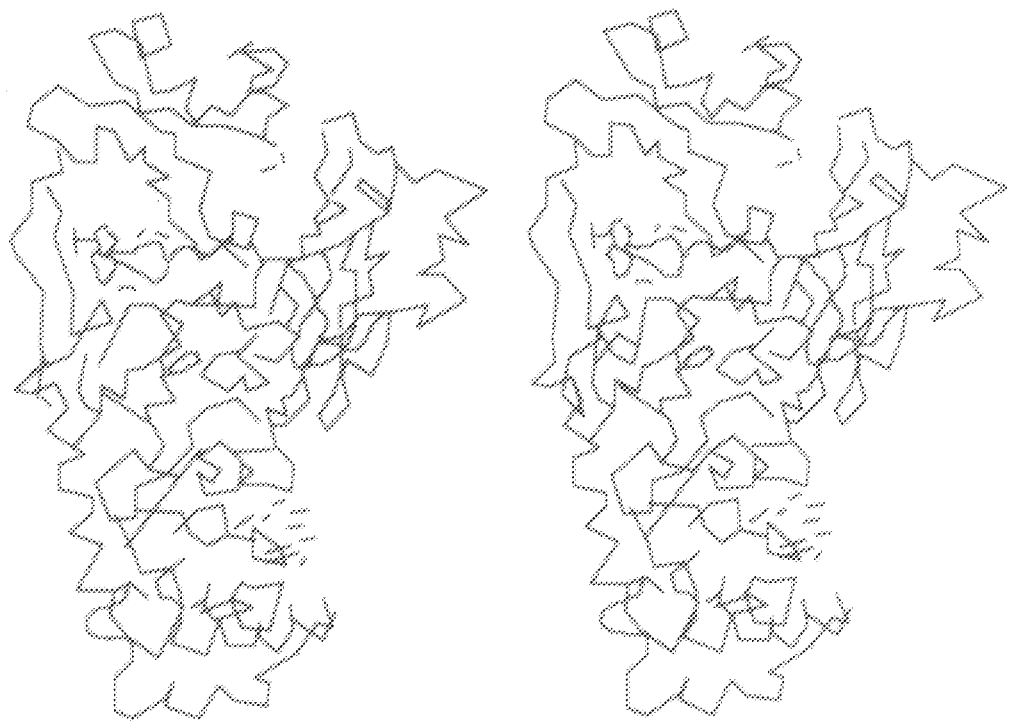
Figure 1C:
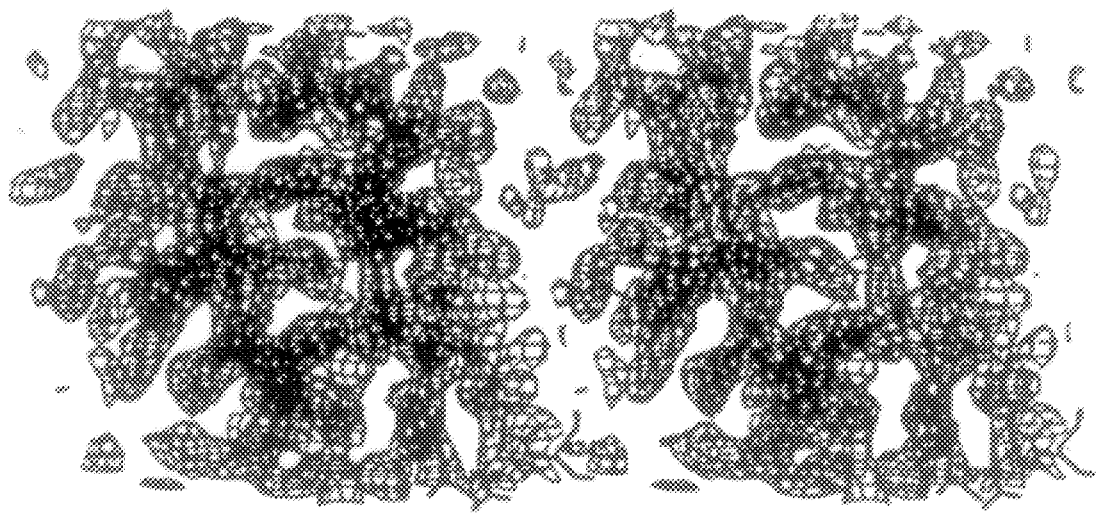

The structure suggests why whole diphtheria toxin is inactive in catalyzing the ADP-ribosylation of EF-2 until the C domain dissociates, in the form of Fragment A, from Fragment B. As shown in FIG. 1b, the active site is formed at the interface between the C domain and the R domain. Entry to the active site is shielded by the 18-residue loop CL2 and the R domain. Thus, in whole diphtheria toxin, the approach of EF-2 ($M_r$=~100K) to the active site is blocked. The active site of whole diphtheria toxin remains accessible to NAD+, however, and catalyzes NAD-glycohydrolysis (a slow side reaction that is probably physiologically insignificant). The lack of secondary structural elements within loop CL2 can allow a substantial movement of main chain atoms of the loop, permitting substrate entry to the active site.

Transmembrane domain

Figure 3A:
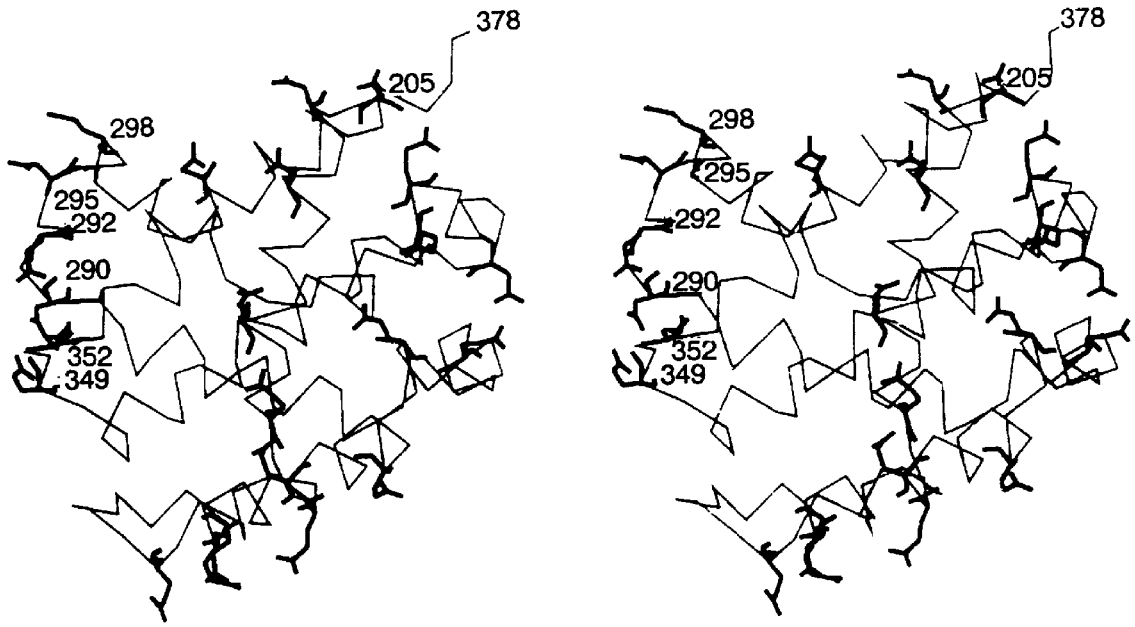
Figure 3B:
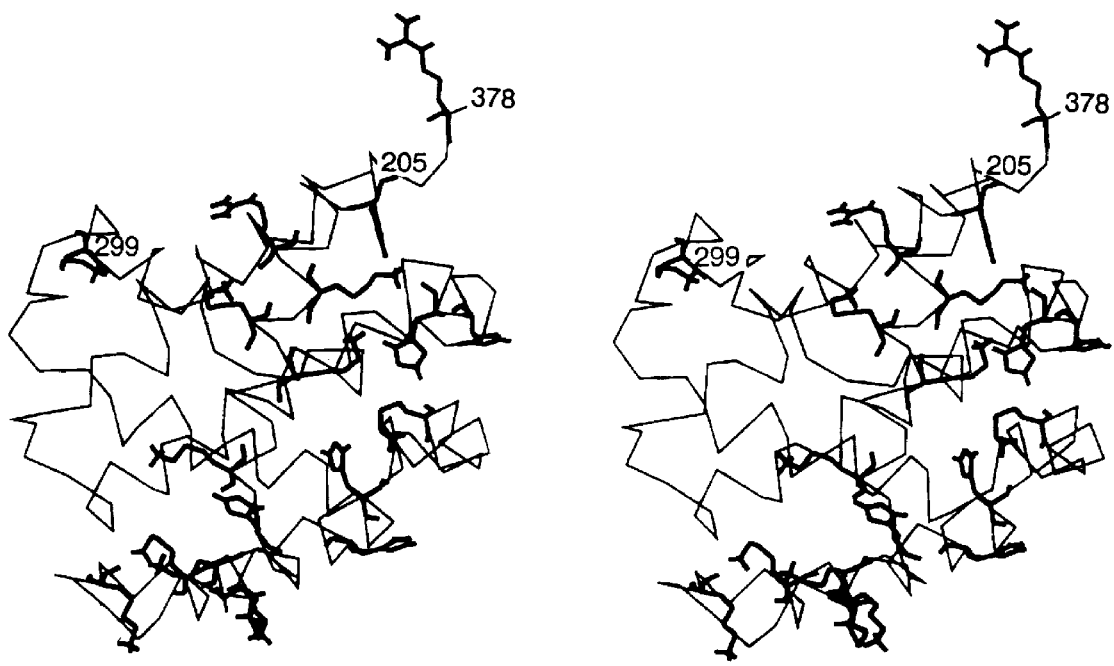

A central, unanswered question about diphtheria toxin is how the low pH milieu of the endosome triggers diphtheria toxin insertion into the endosomal membrane and how this insertion facilitates the translocation of the C domain into the cytoplasm. The structure of the T domain exhibits two features that suggest how it might experience pH-triggered insertion into the membrane. The first is that the T domain is entirely α-helical, similar to the known and proposed transmembrane proteins, and that some of the helices have hydrophobic characteristics more typical of transmembrane helices than of globular proteins (Rees, et al., 1989, *Science* 245:510–513). The nine helices are arranged more or less in three layers, each layer consisting of an antiparallel pair of helices. The two long, C-terminal helices, TH8 and TH9, are unusually apolar and constitute the central core layer. One flanking layer, made up of helices TH5–TH7, also contains hydrophobic helices, TH6 and TH7. The other layer, made up of helices TH1–TH3, is, in contrast, very hydrophilic even compared to globular proteins. The second noteworthy feature of the T domain is the acidic composition of the loops that connect pairs of these helices: both loop TL3 between helices TH5 and TH6, and loop TL5 between hydrophobic helices TH8 and TH9, contain a total of six Asp and Glu residues (FIG. 3a). At neutral pH, these loops are highly charged and water soluble. But at acidic pH, these residues would be at least partially protonated, and hence more nearly neutral and membrane-soluble, especially near the surface of the membrane that has an even higher concentration of protons due to the surface potential (McLaughlin, 1977, *Curr Topics Memb Transport* 9:71–144). Thus the lower pH inside the endosome would tend to render these tip-shaped loops into membrane-soluble "daggers" that would lead the two apolar helix pairs into the membrane.

Other structural characteristics of the T domain suggest that it has the capacity to insert into the membrane and can assist the translocation of the C domain. The first is that the nearly parallel packing of the three helix layers would permit spreading on the membrane surface of the first helix layer (TH1–TH3) if other layers were inserted. The insertion would require local conformational changes in loops, but no alteration of the helices themselves. Also the pronounced hydrophobic asymmetry is compatible with the proposed rearrangement; 15 of 16 Lys and Arg residues and all 6 His residues of the T domain are located on the opposite side from the "dagger" tips (FIG. 3b), making the whole domain a hydrophobic dipole, once the Asp and Glu residues are neutralized. In short, we propose that the hairpin loop TL5 and probably TL3 cross the membrane, where the Asp and Glu residues will once again be charged in the neutral pH of the cytoplasm.

Receptor-binding domain.

The R domain is formed from two β sheets. β strands RB2, RB3, RB5, and RB8 form a four-stranded β sheet that faces a five-stranded β sheet containing β strands RB4, RB6, RB7, RB9, and RB10. RB6 interacts with both β sheets through hydrogen bonds. The connection of the strands is such that the R domain is similar to the jellyroll topology found in many proteins that are exclusively formed from antiparallel β strands (Richardson, 1981, *J Adv Protein Chem* 34:167–339). Jellyroll domains include viral coat proteins, tumor necrosis factor, and the receptor-binding domain of ETA. The domain differs somewhat from a strict jellyroll topology (FIG. 4) in having strand 2 in the "front" sheet, and having a strand 10 in the "back". The R domain also is reminiscent of an immunoglobulin (Ig) variable domain, but differs from the Ig fold in having an "insert" of strands 5 and 6 between 4 and 7, and also in lacking two short strands (C' and C" in FIG. 4) between 4 and 5. The portion of the R domain that resembles a strict jellyroll in topology is the right side as viewed in FIG. 4; and the portion that resembles the Ig variable domain is the left side, the side that is away from the rest of the diphtheria toxin monomer. Conceivably it is this Ig variable-like moiety that is involved in receptor recognition.

The R region structure shows a large loop between the RB8 and RB9 beta strands, constituting residues 496–512 of diphtheria toxin. As it is the only flexible loop of significant size within the HA6DT peptide (Rolf, et al. supra), and it is hydrophilic and exposed, this loop is a likely candidate for the receptor binding region. There is also a significant loop that includes amino acid residues 521–524 and resembles the Ig variable region. This loop can also play a role in receptor-binding, either in combination with the 496–512 loop, or as an alternative binding receptor region. For the loop to assume its correct conformation, additional amino acids surrounding 521–524 would also need to be included, e.g., residues 517–528, 517–525, or 521–528.

In addition there is a loop connecting the last element of secondary structure in the T domain (helix TH9, ending in residue 378) and the first element in the R region (beta strand RB1, beginning with residue 386). This defines the boundary of the R region as occurring between amino acids alanine-379 and threonine-386. An R region polypeptide beginning at this location and extending to the carboxy terminus of diphtheria toxin would comprise between 157 amino acids (predicted MW 17,221) and 150 amino acids (predicted MW 16,480) (Table 2).

TABLE 2

| Initial residue | Mr | # of residues |
|---|---|---|
| A379 | 17,221.4 | 157 |
| Y380 | 17,150.34 | 156 |
| S381 | 16,698.2 | 155 |
| P382 | 16,900.1 | 154 |
| G383 | 16,803.0 | 153 |
| H384 | 16,745.9 | 152 |
| K385 | 16,608.8 | 151 |
| T386 | 16,480.6 | 150 |

The Diphtheria Toxin Dimer

Figure 1D:
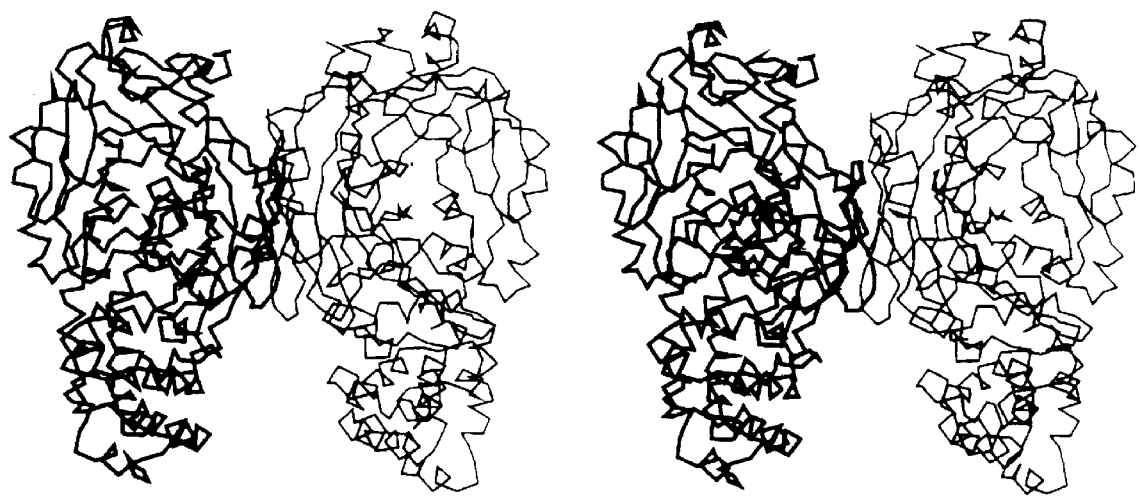

Two monomers associate tightly to form a dimer with an interface between RB1/RB2 of one diphtheria toxin molecule and RB2/RB1 of the other diphtheria toxin molecule related by 2-fold rotation symmetry (FIG. 1d). This interface is one of the three major protein-protein contacts in crystal packing and involves 3 hydrogen bonds per monomer. These hydrogen bonds are well defined since they are formed between main chain N and C atoms of RB1 and RB2. The other interfaces are not common among three different crystal forms. The inability of the dimer to bind to the diphtheria toxin receptor (Carroll, et al., 1986, *Biochemistry* 25:2425–2430) suggests that the dimer interaction sterically blocks the receptor binding domains of each monomer from the receptors on the surface of a target cell. The conformational differences between the monomer within the dimer and the native monomeric diphtheria toxin remain uncertain, but biochemical evidence suggests they are not large. Binding data show that the affinity constant of the dimer for ApUp is the same as that of the monomer, and that the dimer binds 2 ApUp's (Carroll, et al., 1986, *Biochemistry* 25:2425–2430). In addition comparable specific activities of NAD-glycohydrolase activity and affinities for $NAD^+$ were found in the monomer and dimer; and the specific ADP-ribosyltransferase activity of Fragment A released from the dimer after reduction was the same as that from the monomer (Carroll, et al., 1989, *Biochemistry* 25:2425–2430). These findings show that the conformations of the C domain, and of that portion of the R domain interfacing the C domain, are relatively unperturbed in the dimer.

Use

The three-dimensional structure of diphtheria toxin defines the boundary between the R and T domains, and demonstrates that the receptor-binding function is associated with a discrete, compact domain, the R region, most likely localized to residues 496–512 and/or to residues 521–524 (FIG. 5, SEQ ID NO: 1). This R region polypeptide can be useful in developing new vaccines or therapeutic agents against diphtheria.

For instance, a polypeptide of the invention can be used as an immunogen that reacts with diphtheria toxin. It can be administered alone as a purified protein product, or chemically coupled to a carrier substance, such as tetanus toxoid, that would give it even greater stability or greater ability to be transported through the body. The polypeptide can also be combined with an adjuvant to increase its immunogenicity. Possible adjuvants are aluminum salts, bacterial endotoxins or attenuated bacterial strains (e.g., BCG or *Bordetella pertussis*), attenuated viruses, liposomes, or Freund's complete or incomplete adjuvant, which is a water and oil emulsion ± heat-killed *Mycobacterium tuberculosis*. The R region polypeptide can also be expressed in situ after administering by biolistic transfer DNA encoding the R region polypeptide (Tang et al., supra). Immunogens of the invention raise an antibody reaction that can protect the recipient against progression of the disease diphtheria, or against infection by *Corynebacterium diphtheriae*.

Fusion proteins containing the R region polypeptide can be expressed by various carrier vaccine microbes that would give an active immunity against diphtheria toxin, and hence against the disease state caused by diphtheria infection. As part of a fusion protein the R region polypeptide can also be used as a carrier for other less stable immunogens, e.g., polysaccharides or cell surface peptides from pathogens, including but not limited to *Hemophilus influenzae, meningococci*, or *pneumococci*. Elucidation of the boundary between the T and C domains and the R domain also facilitates the design of more effective chimeras of diphtheria toxin.

In addition to use in vaccination, hybrid protein technology in which the diphtheria toxin R region polypeptide is fused to another pharmaceutically useful polypeptide would be a useful method of transporting, stabilizing, and delivering otherwise unstable therapeutics. Besides genetic methods of attaching the polypeptide to a therapeutic, the R region polypeptide can be chemically attached to, and act as a carrier for, delivery of nonpeptide drugs to cells bearing the diphtheria toxin receptor. Chemical groups may be attached by reductive alkylation.

The R region polypeptide of the invention can be useful therapeutically in treating clinical diphtheria. Like antitoxin antibodies, it can block binding of the toxin to diphtheria toxin receptors, possibly eliminating the need for antitoxin therapy or reducing the amount of antitoxin required. Given the problems associated with use of antitoxin antibodies (e.g., the risk of blood-borne infections, such as HIV, and the anti-antitoxin antibodies induced by the use of non-human antibodies) this use of the polypeptides of the invention holds great promise.

Preparation of R region Polypeptides.

Polypeptides of the invention can be synthesized by organic chemical synthesis, produced as a biosynthesized polypeptide, or cleaved from a larger protein containing the amino acid sequences of the invention. For instance, organic chemical synthesis can be performed by conventional methods of automated peptide synthesis, or by classical organic chemical techniques. The R region polypeptide can be cleaved from whole diphtheria toxin protein or from Fragment B, or from a fusion protein containing the R region polypeptide. This could be done with native diphtheria toxin, or alternatively, the DNA encoding diphtheria toxin can be mutated in such a way as to include a protease sensitive site at the TM/R region boundary. The diphtheria toxin protein or Fragment B is then purified, for example by the method of Carroll, et al. (Carroll, et al., 1988. *Meth Enzymol* 165:68–76), and cleaved by proteases specific for the introduced protease-sensitive site.

The R region polypeptide of the invention can be synthesized biologically from genetically-engineered DNA encoding the R region polypeptide. A DNA sequence encoding the polypeptide of the invention can be expressed in a prokaryotic host cell. DNA encoding the R region polypeptide is carried on a vector operably linked to control signals capable of effecting expression in the prokaryotic host. If desired, the coding sequence can contain, at its 5' end, a sequence encoding any of the known signal sequences capable of effecting secretion of the expressed protein into the periplasmic space of the host cell, thereby faciliating recovery of the protein. Prokaryotes most frequently used are represented by various strains of *E. coli*; however, other microbial strains can also be used, e.g., *C. diphtheriae*. Plasmid vectors are used which contain replication origins, selectable markers, and control sequences derived from a species compatible with the microbial host. For example, *E. coli* can be transformed using derivatives of pBR322, a plasmid constructed by Bolivar, et al. (1977, *Gene* 2:95) using fragments derived from three naturally-occurring plasmids, two isolated from species of Salmonella, and one isolated from *E. coli*. pBR322 contains genes for ampicillin and tetracycline resistance, and thus provides multiple selectable markers which can be either retained or destroyed in constructing the desired expression vector. Commonly used prokaryotic expression control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., 198 *Nature* 1056, 1977) and the tryptophan (trp) promoter systems (Goeddel et al., 8 *Nucl. Acids Res.* 4057, 1980) as well as the lambda-derived $P_L$ promoter and N-gene ribosome binding site (Shimatake et al., 292 *Nature* 128, 1981). Examples of microbial strains, vectors, and associated regulatory sequences are listed herein to illustrate, but not to limit, the invention.

One schooled in the art can purify the R region polypeptide of the invention using conventional methods of protein isolation, e.g., methods including but not limited to precipitation, chromatography, immunoadsorption, or affinity techniques. The polypeptide can be purified from starting material using protease-treated diphtheria toxin, or using the cells, or medium of the cells, of a microbial strain genetically engineered to express the R region polypeptide. Purification can also be achieved by making a fusion protein of the R region polypeptide with another recombinant protein, e.g., with a fragment of the maltose binding protein or the glutathione-S-transferase protein, in a manner similar to that described above. These fusion constructs can be made, for example, with the vector pMAL (New England Biolabs) or the vector pGEX-3X or -2T (Pharmacia), which is then purified on affinity columns specific for the maltose binding protein or the glutathione-S-transferase protein, respectively.

Expression of the R region polypeptide

By way of example, a vector expressing the polypeptide of the invention, or a fusion protein including the polypeptide of the invention, can consist of (i) an origin of replication functional in *E. coli* derived from the plasmid pBR322; (ii) a selectable tetracycline resistance gene also derived from pBR322; (iii) a transcription termination region, e.g., the termination of the *E. coli* trp operon (placed at the end of the tetracycline resistance gene to prevent transcriptional read-through into the trp promoter region); (iv) a transcription promoter, e.g., the trp operon promoter, or the diphtheria toxin promoter; (v) the R region protein coding sequence; and (vi) a transcription terminator, e.g., the T1T2 sequence from the ribosomal RNA (rrnB) locus of *E. coli*. The sequences of carrier molecules, the methods used in the synthesis of the DNA sequences, the construction of fusion genes, and the appropriate vectors and expression systems are all well known to those skilled in the art. Similar expression systems can be designed for fusion or non-fusion polypeptides, i.e., for expression of the R region polypeptide alone. These procedures are an example of, but are not limiting on, the methods of the invention.

Administration of a therapeutic composition

The peptides of the invention can be administered to a mammal, particularly a human, by any appropriate method: e.g., orally, parenterally, transdermally, or transmucosally. Administration can be in a sustained release formulation using a biodegradable biocompatible polymer, by on-site delivery using micelles, gels and liposomes, or by transgenic modes. Therapeutic doses can be, but are not necessarily, in the range of 0.1–10.0 mg/kg body weight, or a range that is clinically determined as appropriate by those schooled in the art.

Administration of a vaccine

The R region polypeptide of the invention can be administered directly to a human patient as the immunogen in a vaccine against diphtheria toxin. Alternatively, the polypeptide can be administered in a live attenuated vaccine strain. An administered attenuated organism can proliferate, express the cloned protective protein antigen, and confer protection from both the attenuated organism itself and from the cloned antigen, e.g., the R region polypeptide. Examples of live attenuated vaccine strains include, but are not limited to, BCG, *Salmonella sp*., and *Vibrio cholerae*. Transformation of one of these strains with nucleic acid encoding the R region polypeptide can be accomplished by conventional methods known to those schooled in the art.

The vaccine can also be carried by an attenuated virus, such as adenovirus, herpes virus, or vaccinia virus. Alternatively, the vaccine can be administered by biolistic transfer, which incorporates the DNA encoding an expressible form of the R region polypeptide directly into cells of the vaccinee. An effective final dose of the polypeptide in the patient can be in the range of 1.0–500 μg/kg body weight, or a range that is clinically determined to be appropriate by those schooled in the art.

Other embodiments are within the following claims.

What is claimed is:

1. A DNA encoding a polypeptide consisting of:
a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535; or
s) amino acids 496–524 (all of FIG. 5 (SEQ ID NO: 1)),
wherein said DNA does not encode an amino acid sequence corresponding to amino acids 291 to 378 of FIG. 5 (SEQ ID NO:1) immediately adjacent to the amino terminal end of said polypeptide and said polypeptide is capable of binding a diphtheria toxin sensitive cell.

2. A vector comprising the DNA of claim 1.

3. A host cell comprising the DNA of claim 1.

4. The cell of claim 3, wherein said cell expresses said polypeptide.

5. The vector of claim 2, wherein said DNA sequence is under the transcriptional control of a heterologous promoter.

6. The vector of claim 2, wherein said DNA is linked to a signal sequence.

7. An essentially homogeneous population of host cells, each of which comprises the DNA of claim 1.

8. An essentially pure preparation of nucleic acid, said nucleic acid comprising a sequence encoding a polypeptide consisting of:
a) amino acids 379–535;
b) amino acids 380–535;
c) amino acids 381–535;
d) amino acids 382–535;
e) amino acids 383–535;

f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535; or
s) amino acids 496–524 (all of FIG. 5 (SEQ ID NO: 1)), wherein said nucleic acid does not encode an amino acid sequence corresponding to amino acids 291 to 378 of FIG. 5 (SEQ ID NO:1) immediately adjacent to the amino terminal end of said polypeptide and said polypeptide is capable of binding a diphtheria toxin sensitive cell.

9. A method of preparation of a polypeptide comprising providing the cell of claim 4,
growing said cell in a medium to form a population of cells that express said polypeptide, and
obtaining said polypeptide from said population of cells or said medium.

10. A method of making a polypeptide consisting of
a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512:
r) amino acids 496–535; or
s) amino acids 496–524 (all of FIG. 5 (SEQ ID NO: 1)), comprising synthesizing said polypeptide biologically by expression from genetically-engineered DNA encoding said polypeptide.

11. A DNA encoding a fusion polypeptide consisting of (1) a first sequence corresponding to
a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535; or
s) amino acids 496–524 (all of FIG. 5 (SEQ ID NO: 1)), linked by a peptide bond to (2) a second sequence, provided that said fusion polypeptide does not comprise amino acids 291 to 378 of FIG. 5 (SEQ ID NO:1) immediately adjacent to the amino terminal end of said first sequence.

12. A host cell comprising the DNA of claim 11.

13. The cell of claim 12, wherein said cell expresses said polypeptide.

14. The DNA of claim 1, wherein said polypeptide consists of
a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535; or
s) amino acids 496–524 (all of FIG. 5 (SEQ ID NO: 1)).

15. The essentially pure preparation of nucleic acid of claim 8, wherein said polypeptide consists of
a) amino acids 379–535;
b) amino acids 380–535;
c) amino acids 381–535;
d) amino acids 382–535;
e) amino acids 383–535;
f) amino acids 384–535;
g) amino acids 385–535;
h) amino acids 386–535;
i) amino acids 496–512;
j) amino acids 379–512;
k) amino acids 380–512;
l) amino acids 381–512;
m) amino acids 382–512;
n) amino acids 383–512;
o) amino acids 384–512;
p) amino acids 385–512;
q) amino acids 386–512;
r) amino acids 496–535; or
s) amino acids 496–524 (all of FIG. 5 (SEQ ID NO: 1)).

* * * * *

UNITED STATES PATENT AND TRADEMARK OFFICE
CERTIFICATE OF CORRECTION

PATENT NO. : 5,843,711 B2  
APPLICATION NO. : 08/552248  
DATED : December 1, 1998  
INVENTOR(S) : Collier et al.

Page 1 of 1

It is certified that error appears in the above-identified patent and that said Letters Patent is hereby corrected as shown below:

In the Specification

Please delete the paragraph beginning at Column 1, Line 8, and replace it with the following:
This invention was made with government support under AI022021, AI022848, GM031299 and GM039588 awarded by the National Institutes of Health. The government has certain rights in the invention.

Signed and Sealed this  
Tenth Day of December, 2024

Katherine Kelly Vidal  
*Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 1942
( B ) TYPE: nucleic acid
( C ) STRANDEDNESS: double
( D ) TOPOLOGY: linear ( x i ) SEQUENCE DESCRIPTION: SEQ ID NO: 1:

```
CCGGCGTTGC GTATCCAGTG GCTACACTCA GGTTGTAATG ATTGGGATGA TGTACCTGAT     60

CTGAGAGCGA TTAAAAACTC ATTGAGGAGT AGGTCCCGAT TGGTTTTTGC TAGTGAAGCT    120

TAGCTAGCTT TCCCCATGTA ACCAATCTAT CAAAAAAGGG CATTGATTTC AGAGCACCCT    180

TATAATTAGG ATAGCTTTAC CTAATTATTT TATGAGTCCT GGTAAGGGGA TACGTTGTGA    240

GCAGAAAACT GTTTGCGTCA ATCTTAATAG GGGCGCTACT GGGGATAGGG GCCCCACCTT    300

CAGCCCATGC A                                                         311

GGC GCT GAT GAT GTT GTT GAT TCT TCT AAA TCT TTT GTG ATG GAA AAC      359
Gly Ala Asp Asp Val Val Asp Ser Ser Lys Ser Phe Val Met Glu Asn
1               5                   10                  15
```

```
TTT TCT TCG TAC CAC GGG ACT AAA CCT GGT TAT GTA GAT TCC ATT CAA      407
Phe Ser Ser Tyr His Gly Thr Lys Pro Gly Tyr Val Asp Ser Ile Gln
        20              25              30

AAA GGT ATA CAA AAG CCA AAA TCT GGT ACA CAA GGA AAT TAT GAC GAT      455
Lys Gly Ile Gln Lys Pro Lys Ser Gly Thr Gln Gly Asn Tyr Asp Asp
        35              40              45

GAT TGG AAA GGG TTT TAT AGT ACC GAC AAT AAA TAC GAC GCT GCG GGA      503
Asp Trp Lys Gly Phe Tyr Ser Thr Asp Asn Lys Tyr Asp Ala Ala Gly
        50              55              60

TAC TCT GTA GAT AAT GAA AAC CCG CTC TCT GGA AAA GCT GGA GGC GTG      551
Tyr Ser Val Asp Asn Glu Asn Pro Leu Ser Gly Lys Ala Gly Gly Val
65              70              75              80

GTC AAA GTG ACG TAT CCA GGA CTG ACG AAG GTT CTC GCA CTA AAA GTG      599
Val Lys Val Thr Tyr Pro Gly Leu Thr Lys Val Leu Ala Leu Lys Val
                85              90              95

GAT AAT GCC GAA ACT ATT AAG AAA GAG TTA GGT TTA AGT CTC ACT GAA      647
Asp Asn Ala Glu Thr Ile Lys Lys Glu Leu Gly Leu Ser Leu Thr Glu
            100             105             110

CCG TTG ATG GAG CAA GTC GGA ACG GAA GAG TTT ATC AAA AGG TTC GGT      695
Pro Leu Met Glu Gln Val Gly Thr Glu Glu Phe Ile Lys Arg Phe Gly
        115             120             125

GAT GGT GCT TCG CGT GTA GTG CTC AGC CTT CCC TTC GCT GAG GGG AGT      743
Asp Gly Ala Ser Arg Val Val Leu Ser Leu Pro Phe Ala Glu Gly Ser
    130             135             140

TCT AGC GTT GAA TAT ATT AAT AAC TGG GAA CAG GCG AAA GCG TTA AGC      791
Ser Ser Val Glu Tyr Ile Asn Asn Trp Glu Gln Ala Lys Ala Leu Ser
145             150             155             160

GTA GAA CTT GAG ATT AAT TTT GAA ACC CGT GGA AAA CGT GGC CAA GAT      839
Val Glu Leu Glu Ile Asn Phe Glu Thr Arg Gly Lys Arg Gly Gln Asp
                165             170             175

GCG ATG TAT GAG TAT ATG GCT CAA GCC TGT GCA GGA AAT CGT GTC AGG      887
Ala Met Tyr Glu Tyr Met Ala Gln Ala Cys Ala Gly Asn Arg Val Arg
            180             185             190

CGA TCA GTA GGT AGC TCA TTG TCA TGC ATA AAT CTT GAT TGG GAT GTC      935
Arg Ser Val Gly Ser Ser Leu Ser Cys Ile Asn Leu Asp Trp Asp Val
        195             200             205

ATA AGG GAT AAA ACT AAG ACA AAG ATA GAG TCT TTG AAA GAG CAT GGC      983
Ile Arg Asp Lys Thr Lys Thr Lys Ile Glu Ser Leu Lys Glu His Gly
    210             215             220

CCT ATC AAA AAT AAA ATG AGC GAA AGT CCC AAT AAA ACA GTA TCT GAG     1031
Pro Ile Lys Asn Lys Met Ser Glu Ser Pro Asn Lys Thr Val Ser Glu
225             230             235             240

GAA AAA GCT AAA CAA TAC CTA GAA GAA TTT CAT CAA ACG GCA TTA GAG     1079
Glu Lys Ala Lys Gln Tyr Leu Glu Glu Phe His Gln Thr Ala Leu Glu
                245             250             255

CAT CCT GAA TTG TCA GAA CTT AAA ACC GTT ACT GGG ACC AAT CCT GTA     1127
His Pro Glu Leu Ser Glu Leu Lys Thr Val Thr Gly Thr Asn Pro Val
            260             265             270

TTC GCT GGG GCT AAC TAT GCG GCG TGG GCA GTA AAC GTT GCG CAA GTT     1175
Phe Ala Gly Ala Asn Tyr Ala Ala Trp Ala Val Asn Val Ala Gln Val
        275             280             285

ATC GAT AGC GAA ACA GCT GAT AAT TTG GAA AAG ACA ACT GCT GCT CTT     1223
Ile Asp Ser Glu Thr Ala Asp Asn Leu Glu Lys Thr Thr Ala Ala Leu
    290             295             300

TCG ATA CTT CCT GGT ATC GGT AGC GTA ATG GGC ATT GCA GAC GGT GCC     1271
Ser Ile Leu Pro Gly Ile Gly Ser Val Met Gly Ile Ala Asp Gly Ala
305             310             315             320

GTT CAC CAC AAT ACA GAA GAG ATA GTG GCA CAA TCA ATA GCT TTA TCG     1319
Val His His Asn Thr Glu Glu Ile Val Ala Gln Ser Ile Ala Leu Ser
                325             330             335
```

-continued

| | | | | | | | | | | | | | | | | |
|---|---|---|---|---|---|---|---|---|---|---|---|---|---|---|---|---|
| TCT | TTA | ATG | GTT | GCT | CAA | GCT | ATT | CCA | TTG | GTA | GGA | GAG | CTA | GTT | GAT | 1367 |
| Ser | Leu | Met | Val | Ala | Gln | Ala | Ile | Pro | Leu | Val | Gly | Glu | Leu | Val | Asp | |
| | | | 340 | | | | | 345 | | | | | 350 | | | |
| ATT | GGT | TTC | GCT | GCA | TAT | AAT | TTT | GTA | GAG | AGT | ATT | ATC | AAT | TTA | TTT | 1415 |
| Ile | Gly | Phe | Ala | Ala | Tyr | Asn | Phe | Val | Glu | Ser | Ile | Ile | Asn | Leu | Phe | |
| | | 355 | | | | | 360 | | | | | 365 | | | | |
| CAA | GTA | GTT | CAT | AAT | TCG | TAT | AAT | CGT | CCC | GCG | TAT | TCT | CCG | GGG | CAT | 1463 |
| Gln | Val | Val | His | Asn | Ser | Tyr | Asn | Arg | Pro | Ala | Tyr | Ser | Pro | Gly | His | |
| | 370 | | | | | 375 | | | | | 380 | | | | | |
| AAA | ACG | CAA | CCA | TTT | CTT | CAT | GAC | GGG | TAT | GCT | GTC | AGT | TGG | AAC | ACT | 1511 |
| Lys | Thr | Gln | Pro | Phe | Leu | His | Asp | Gly | Tyr | Ala | Val | Ser | Trp | Asn | Thr | |
| 385 | | | | | 390 | | | | | 395 | | | | | 400 | |
| GTT | GAA | GAT | TCG | ATA | ATC | CGA | ACT | GGT | TTT | CAA | GGG | GAG | AGT | GGG | CAC | 1559 |
| Val | Glu | Asp | Ser | Ile | Ile | Arg | Thr | Gly | Phe | Gln | Gly | Glu | Ser | Gly | His | |
| | | | | 405 | | | | | 410 | | | | | 415 | | |
| GAC | ATA | AAA | ATT | ACT | GCT | GAA | AAT | ACC | CCG | CTT | CCA | ATC | GCG | GGT | GTC | 1607 |
| Asp | Ile | Lys | Ile | Thr | Ala | Glu | Asn | Thr | Pro | Leu | Pro | Ile | Ala | Gly | Val | |
| | | | 420 | | | | | 425 | | | | | 430 | | | |
| CTA | CTA | CCG | ACT | ATT | CCT | GGA | AAG | CTG | GAC | GTT | AAT | AAG | TCC | AAG | ACT | 1655 |
| Leu | Leu | Pro | Thr | Ile | Pro | Gly | Lys | Leu | Asp | Val | Asn | Lys | Ser | Lys | Thr | |
| | | 435 | | | | | 440 | | | | | 445 | | | | |
| CAT | ATT | TCC | GTA | AAT | GGT | CGG | AAA | ATA | AGG | ATG | CGT | TGC | AGA | GCT | ATA | 1703 |
| His | Ile | Ser | Val | Asn | Gly | Arg | Lys | Ile | Arg | Met | Arg | Cys | Arg | Ala | Ile | |
| | 450 | | | | | 455 | | | | | 460 | | | | | |
| GAC | GGT | GAT | GTA | ACT | TTT | TGT | CGC | CCT | AAA | TCT | CCT | GTT | TAT | GTT | GGT | 1751 |
| Asp | Gly | Asp | Val | Thr | Phe | Cys | Arg | Pro | Lys | Ser | Pro | Val | Tyr | Val | Gly | |
| 465 | | | | | 470 | | | | | 475 | | | | | 480 | |
| AAT | GGT | GTG | CAT | GCG | AAT | CTT | CAC | GTG | GCA | TTT | CAC | AGA | AGC | AGC | TCG | 1799 |
| Asn | Gly | Val | His | Ala | Asn | Leu | His | Val | Ala | Phe | His | Arg | Ser | Ser | Ser | |
| | | | | 485 | | | | | 490 | | | | | 495 | | |
| GAG | AAA | ATT | CAT | TCT | AAT | GAA | ATT | TCG | TCG | GAT | TCC | ATA | GGC | GTT | CTT | 1847 |
| Glu | Lys | Ile | His | Ser | Asn | Glu | Ile | Ser | Ser | Asp | Ser | Ile | Gly | Val | Leu | |
| | | | 500 | | | | | 505 | | | | | 510 | | | |
| GGG | TAC | CAG | AAA | ACA | GTA | GAT | CAC | ACC | AAG | GTT | AAT | TCT | AAG | CTA | TCG | 1895 |
| Gly | Tyr | Gln | Lys | Thr | Val | Asp | His | Thr | Lys | Val | Asn | Ser | Lys | Leu | Ser | |
| | | 515 | | | | | 520 | | | | | 525 | | | | |
| CTA | TTT | TTT | GAA | ATC | AAA | AGC | TGAAAGGTAG | TGGGGTCGTG | TGCCGG | | | | | | | 1942 |
| Leu | Phe | Phe | Glu | Ile | Lys | Ser | | | | | | | | | | |
| | 530 | | | | | 535 | | | | | | | | | | |